(12) United States Patent
Marvaniya et al.

(10) Patent No.: US 11,275,778 B2
(45) Date of Patent: Mar. 15, 2022

(54) CONTENT MARSHALING USING BIOMETRIC DATA

(71) Applicant: International Business Machines Corporation, Armonk, NY (US)

(72) Inventors: Smitkumar Narotambhai Marvaniya, Bangalore (IN); Malolan Chetlur, Bangalore (IN); Bikram Sengupta, Bangalore (IN); Renuka Sindhgatta, Bangalore (IN); Mukesh Kumar Mohania, Forrest (AU)

(73) Assignee: International Business Machines Corporation, Armonk, NY (US)

( * ) Notice: Subject to any disclaimer, the term of this patent is extended or adjusted under 35 U.S.C. 154(b) by 183 days.

(21) Appl. No.: 16/209,076

(22) Filed: Dec. 4, 2018

(65) Prior Publication Data
US 2020/0175057 A1 Jun. 4, 2020

(51) Int. Cl.
| G06F 16/00 | (2019.01) |
| G06F 16/435 | (2019.01) |
| A61B 5/16 | (2006.01) |
| G06K 9/00 | (2022.01) |
| G06F 3/01 | (2006.01) |

(52) U.S. Cl.
CPC ........... *G06F 16/436* (2019.01); *A61B 5/165* (2013.01); *G06F 3/013* (2013.01); *G06K 9/00026* (2013.01); *G06K 9/00302* (2013.01); *G06K 9/00335* (2013.01)

(58) Field of Classification Search
None
See application file for complete search history.

(56) References Cited

U.S. PATENT DOCUMENTS

| 7,657,652 | B1 | 2/2010 | Balaji |
| 10,365,716 | B2* | 7/2019 | Aimone ................. A61B 5/378 |
| RE48,056 | E * | 6/2020 | Hoffberg ................ G16H 40/67 |
| 10,884,493 | B2* | 1/2021 | Parshionikar .......... G06F 3/012 |
| 2014/0223462 | A1 | 8/2014 | Aimone et al. |
| 2014/0347265 | A1* | 11/2014 | Aimone ................ H04W 4/029 345/156 |
| 2016/0063883 | A1 | 3/2016 | Jeyanandarajan |
| 2016/0170996 | A1* | 6/2016 | Frank ................ G06F 16/24578 707/748 |

(Continued)

FOREIGN PATENT DOCUMENTS

WO 2017081476 A1 5/2017

OTHER PUBLICATIONS

Metz, R., Controlling VR with Your Mind, MIT Technology Review, https://www.technologyreview.com/s/603896/controlling-vr-with-your-mind/, Mar. 22, 2017.

(Continued)

*Primary Examiner* — Farhan M Syed
(74) *Attorney, Agent, or Firm* — Ryan, Mason & Lewis, LLP (57) ABSTRACT

Methods, systems, and computer program products for content marshaling using biometric data are provided herein. A computer-implemented method includes estimating a cognitive state of a user based at least in part on analyzing one or more sets of biometric data pertaining to the user; dynamically compiling multi-modal content for the user based at least in part on (i) the estimated cognitive state of the user, (ii) one or more user parameters, and (iii) content availability information; and outputting the compiled content to the user via one or more devices.

10 Claims, 7 Drawing Sheets

(56) References Cited

U.S. PATENT DOCUMENTS

| | | | | |
|---|---|---|---|---|
| 2016/0170998 | A1* | 6/2016 | Frank | H04W 4/021 |
| | | | | 707/748 |
| 2016/0203726 | A1 | 7/2016 | Hibbs et al. | |
| 2016/0358488 | A1 | 12/2016 | Canter et al. | |
| 2018/0133431 | A1* | 5/2018 | Malchano | A61N 1/36036 |
| 2018/0348861 | A1* | 12/2018 | Uscinski | G06F 3/012 |
| 2019/0347801 | A1* | 11/2019 | Ellison | G06T 5/50 |
| 2019/0384392 | A1* | 12/2019 | Aimone | G06F 3/015 |
| 2019/0392145 | A1* | 12/2019 | Komogortsev | G06F 21/32 |
| 2020/0249752 | A1* | 8/2020 | Parshionikar | G06F 3/04817 |

OTHER PUBLICATIONS

Connor-Simons, A., Brain-controlled Robots, MIT News, http://news.mit.edu/2017/brain-controlled-robots-0306, Mar. 3, 2017.
Design to Improve Life, PsychicVR, http://award.designtoimprovelife.dk/nomination/2133, Dec. 3, 2018.
Imbert et al., A Multiagent Extension for Virtual Reality Based Intelligent Tutoring System, 2007.
Whitmire et al., EyeContact: scleral coil eye tracking for virtual reality, ISWC, 2016.
Medium, Things to keep in mind while designing digital content, https://medium.com/@getmagicbox/things-to-keep-in-mind-while-designing-digital-content-fa4e7d36f917, Mar. 21, 2017.
Patel, N., The Nine Ingredients that Make Great Content, https://blog.kissmetrics.com/ingredients-of-great-content/, Nov. 16, 2018.
Bedi, B., 3 Things to Remember while Creating Personalized Digital Content, RockOnIt, https://www.rockonit.com/blog/3-things-to-remember-while-creating-personalized-digital-content, Jul. 15, 2016.

* cited by examiner

CONTENT MARSHALING USING BIOMETRIC DATA

FIELD

The present application generally relates to information technology and, more particularly, to content management across systems.

BACKGROUND

Generally, for user learning experiences to be beneficial and/or effective, the content provided to the user is engaging to both the mind and the senses of the user. By way of illustration, learners can perceive a concept in content through one or more of the user's senses (via video, images, speech and/or sound, for example), and learners can also imagine the concept through abstractions and details (text descriptions, equations, etc.) included in the content. However, existing content provisioning systems do not monitor or analyze the perception-based or imagination-based engagement of the user during learning. Highly perceptive content with no imagination-based engagement can lead to boredom for the user, while highly imaginative content with minimal perceptive-based engagement can lead to confusion and/or omission of concept learning.

SUMMARY

In one embodiment of the present invention, techniques for content marshaling using biometric data are provided. An exemplary computer-implemented method can include estimating a cognitive state of a user based at least in part on analyzing one or more sets of biometric data pertaining to the user; dynamically compiling multi-modal content for the user based at least in part on (i) the estimated cognitive state of the user, (ii) one or more user parameters, and (iii) content availability information; and outputting the compiled content to the user via one or more devices.

In another embodiment of the invention, an exemplary computer-implemented method can also include estimating the cognitive state of the user by learning at least one classifier based at least in part on one or more biometric data feature representations, and applying the at least one classifier to the one or more sets of biometric data.

Another embodiment of the invention or elements thereof can be implemented in the form of a computer program product tangibly embodying computer readable instructions which, when implemented, cause a computer to carry out a plurality of method steps, as described herein. Furthermore, another embodiment of the invention or elements thereof can be implemented in the form of a system including a memory and at least one processor that is coupled to the memory and configured to perform noted method steps. Yet further, another embodiment of the invention or elements thereof can be implemented in the form of means for carrying out the method steps described herein, or elements thereof; the means can include hardware module(s) or a combination of hardware and software modules, wherein the software modules are stored in a tangible computer-readable storage medium (or multiple such media).

These and other objects, features and advantages of the present invention will become apparent from the following detailed description of illustrative embodiments thereof, which is to be read in connection with the accompanying drawings.

DETAILED DESCRIPTION

As described herein, an embodiment of the present invention includes content marshaling using biometric data. For example, one or more embodiments of the invention includes marshaling dynamic and/or fluid content to a user, wherein the content includes a balance of perception-based engagement and imagination-based engagement for the user, so as to improve overall user engagement and user experience.

Additionally, at least one embodiment of the invention includes delivering an optimal form of learning content for a particular user, wherein the content can include text content, audio content, video content, augmented reality (AR) content and/or virtual reality (VR) content. Such an embodiment can include estimating a cognitive state of the learner/user, wherein the cognitive state includes a perception index and an imagination index. More specifically, at least one embodiment of the invention includes estimating an imagination index and a perception index attributed to a user, which can include using biometric data such as eye gaze data, brain signal data, and/or body movement data.

Additionally, based at least in part on such an estimated imagination index and such an estimated perception index, one or more embodiments of the invention can include dynamically marshaling (that is, strategically compiling and/or arranging) particular learning content for the user (so as to improve the user's learning experience). As further detailed herein, such marshaling can also be based in part on user and content information such as, for example, user engagement information, user models, one or more content libraries, and/or user pedagogy information.

As used herein, perception refers to the ability to see, hear, or become aware of something through the senses, and a perception index estimates the involvement of one or more of the senses in connection with a user engaging with content. Additionally, as used herein, imagination refers to forming ideas, thoughts or images of things not necessarily present to the senses, and an imagination index estimates the creative involvement of the user's mind in connection with the user engaging with content.

Figure 1:
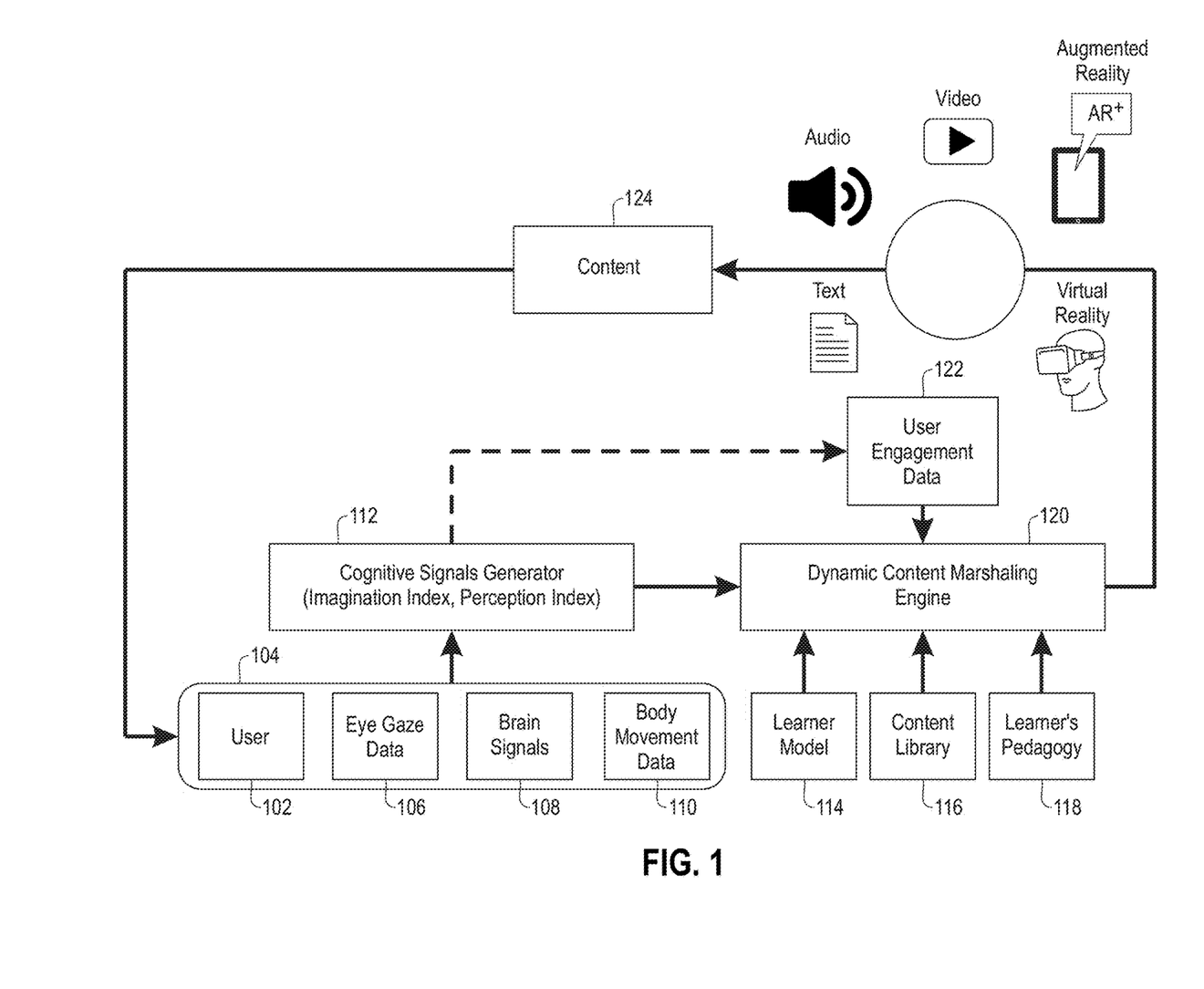
FIG. 1 is a diagram illustrating system architecture, according to an exemplary embodiment of the invention.

FIG. 1 is a diagram illustrating system architecture, according to an embodiment of the invention. By way of illustration, FIG. 1 depicts a user 102 and a set of user-related inputs 104, which include eye gaze data 106, brain signals 108, and body movement data 110. In one or more embodiments of the invention, eye gaze data 106 can be captured through eye gaze tracker devices and/or specialized cameras focused on a person, which help in extracting the eye gaze patterns in terms of fixations and saccades. Brain signals 108 can be captured through one or more brain sensing devices such as an electroencephalography (EEG), an electrophysiological technique, an electrooculography (EOG), an electromyography (EMG), an electrocardiography (EKG), event-related potential (ERP), etc. Additionally, body movement data 110 can be inferred through gyro and/or accelerometer sensor-enabled smart bands, smartwatches and/or smart wearables, which help in tracking user body movements in terms of speed and orientation.

Based at least in part on the user-related inputs 104, a cognitive signals generator 112 generates an imagination index and a perception index attributed to user 102, and provides the generated indices to dynamic content marshaling engine 120. Specifically, to infer the imagination index and the perception index of a user 102, the cognitive signals generator 112 senses data related to eye gaze 106, brain signals 108, and body movement 110 attributed to the user 102. In one or more embodiments of the invention, the user 102 is a part of the learning activity by interacting with provided content (such as content 124, for example).

Additionally, the generated indices can also be provided to a user engagement data component 122, which also provides input to the dynamic content marshaling engine 120. User engagement data 122 can include user engagement and/or behavior-related features such as an average session length metric, a diligence score metric (which can be a function of login frequency, average session length, length of content video, etc.), a reflective score metric (which can be a function of the number of rewind events), an impatience score metric (which can be a function of the number of forward seek events), an amount completed metric (which represents the fraction of a content video watched by the user), etc., which capture how the user 102 interacted with the data and/or content.

The dynamic content marshaling engine 120 can also receive, as inputs, a learner/user model 114, a content library 116, and the learner's/user's pedagogy 118. The learner/user model, by way of example, can include personalization parameters specific to user 102 that include content difficulty preferences, cognitive load information, resource information (such as related to user device power, etc.), budget and/or time information, mood information, mastery level information with respect to multiple types of content, etc.

Additionally, the learner/user model 114 can contain information pertaining to the current state of user 102, and it can update such information based on user interaction with additional cognitive content. Also, the content library 116 can contain all forms of relevant content available for use, wherein such content can include, for example, text content, audio content, video content, augmented reality content, and/or virtual reality content. Further, user's/learner's pedagogy information 118 can include information such as identification of known and unknown concepts for user 102, as well as identification of the user's learning styles and/or preferences (such as, for example, depth-first searching or breadth-first searching content exploration). By way of example, if a user knows a certain concept, and a tutor wishes to teach the user one or more unknown concepts, the user's imagination index may be changed from higher to lower, whereas the user's perception index may be changed from lower to higher, and content can be marshaled and provided to the user accordingly.

Based at least in part on the above-noted and illustrated inputs, the dynamic content marshaling engine 120 generates an output that includes personalized multi-modal content 124 for user 102. Specifically, in one or more embodiments of the invention, the dynamic content marshaling engine 120 takes the current state of the user's (102) cognitive signals in the form of imagination index and perception index (generated by cognitive signals generator 112) as an input along with the learner/user model 114, user engagement data 122, content library 116, and learner's/user's pedagogy information 118. Using such inputs, the dynamic content marshaling engine 120 identifies the most advantageous form of content 124 (text, audio, video, augmented reality, and/or virtual reality) for the given cognitive state of the user 102.

Additionally, the dynamic content marshaling engine 120 can estimate the change of content form by learning a classifier which takes, as input, change in the user's aggregated imagination index, change in the user's aggregated perception index, the user engagement data 122, and the learner's/user's pedagogy information 118, and predicts the form(s) of the content such that the user experience and user engagement is satisfactory.

Figure 2:
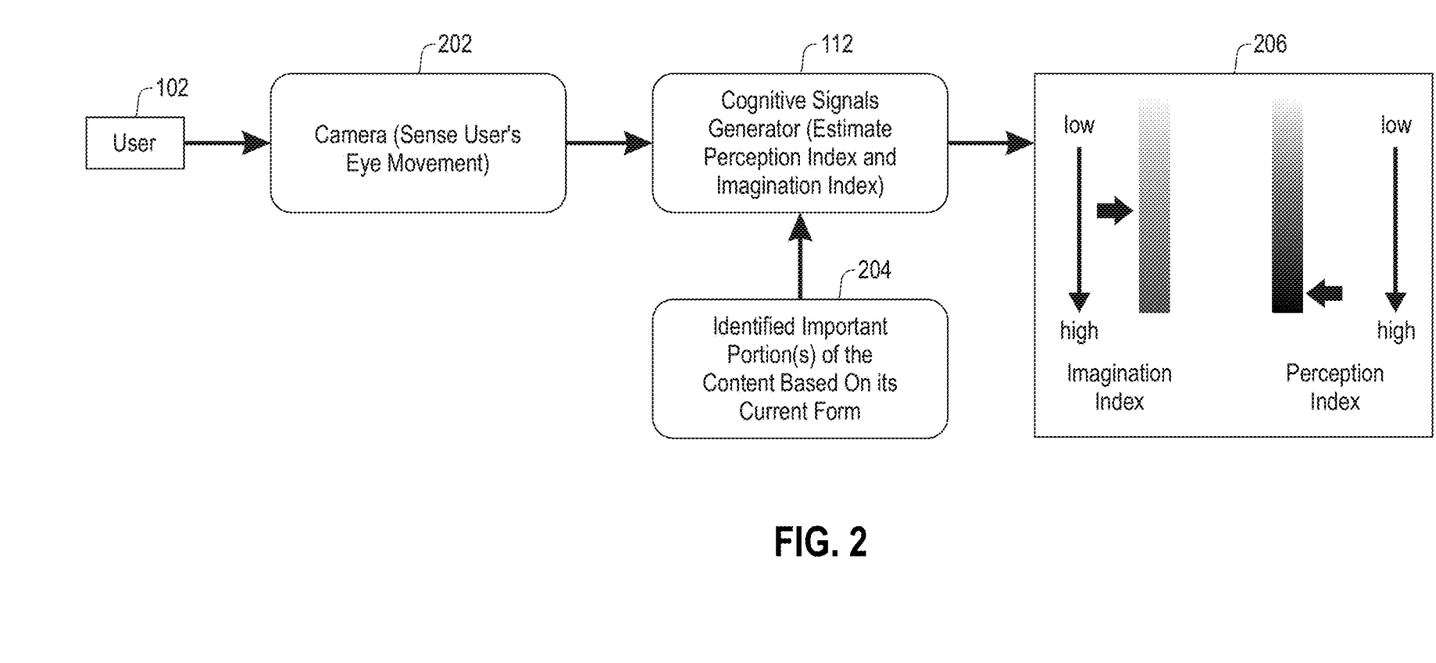
FIG. 2 is a diagram illustrating estimation of the cognitive state of a user using eye gaze data, according to an exemplary embodiment of the invention.

FIG. 2 is a diagram illustrating estimation of the cognitive state of a user using eye gaze data, according to an exemplary embodiment of the invention. By way of illustration, the eye movement of user 102 can be tracked using camera 202, and based on the analysis of that eye movement data, one or more embodiments of the invention can include identifying whether the user 102 is looking at some portion of the content which might not be important for the user 102 to concentrate on. Such a determination, as illustrated in FIG. 2, can be made in conjunction with component 204, which includes identified important portion(s) of the content in question based on the content's current form.

In one or more embodiments of the invention, important content portions 204 can be inferred using static content-related features and/or dynamic content-related features. Static content-related features can be inferred, for example, by analyzing the content (such as a textbook, for example), as well as analyzing frequently asked questions (FAQs) related to the content, important keywords/phrases, etc., without considering the user's interactions with the content. Dynamic content-related features can be inferred, for example, by considering data such as the average session length, the average skip time duration, user behavior-related metrics, etc., which capture the user's engagement and/or interactions with the content.

Also, based at least in part on the user's pedagogy information and the eye gaze data captured via camera 202, the cognitive signals generator 112 can determine and/or estimate an output 206 including an imagination index and a perception index for user 102.

As detailed herein, one or more embodiments of the invention include techniques for estimating a perception index and an imagination index for a given user. By way of example, such an embodiment can include learning and implementing the multiple classifiers. Using inputs such as EEG brainwave patterns, eye tracking patterns, body movement data, and one or more personalization parameters, a feature representation can be represented as follows: $<f_1^{brain}, f_2^{brain}, \ldots, f_n^{brain}, f_1^{eye}, f_2^{eye}, \ldots, f_k^{eye}, f_1^{body\ movement}, f_2^{body\ movement}, \ldots, f_l^{body\ movement}, f_1^{personalization}, \ldots, f_m^{personalization}>$.

Additionally, at least one embodiment of the invention can include learning a classifier which takes the above-noted feature representation as an input and predicts an imagination index: $\phi^{imagination}(u)$ for a given user based thereon. Additionally, such an embodiment can also include learning a classifier which takes the above-noted feature representation as an input and predicts a perception index: $\phi^{perception}(u)$ for the given user based thereon.

Accordingly, as detailed herein, one or more embodiments of the invention include multiple stages of action. In a first such stage, the system asks the user to interact with the system during a training phase, which helps in capturing eye gaze data, brain signals, and body movement data, and a teacher and/or subject-matter-expert can further provide ground truth information which will be used in modeling the training phase. As such, the training phase captures user biometric information in terms of brain signal-related features, eye gaze-related features, body movement-related features, and uses such features for building imagination index and perception index classifiers. In a second stage, the system captures the feature representations while the user is interacting with provided content, and classifies the user's cognitive state in terms of a perception index and an imagination index.

Figure 3:
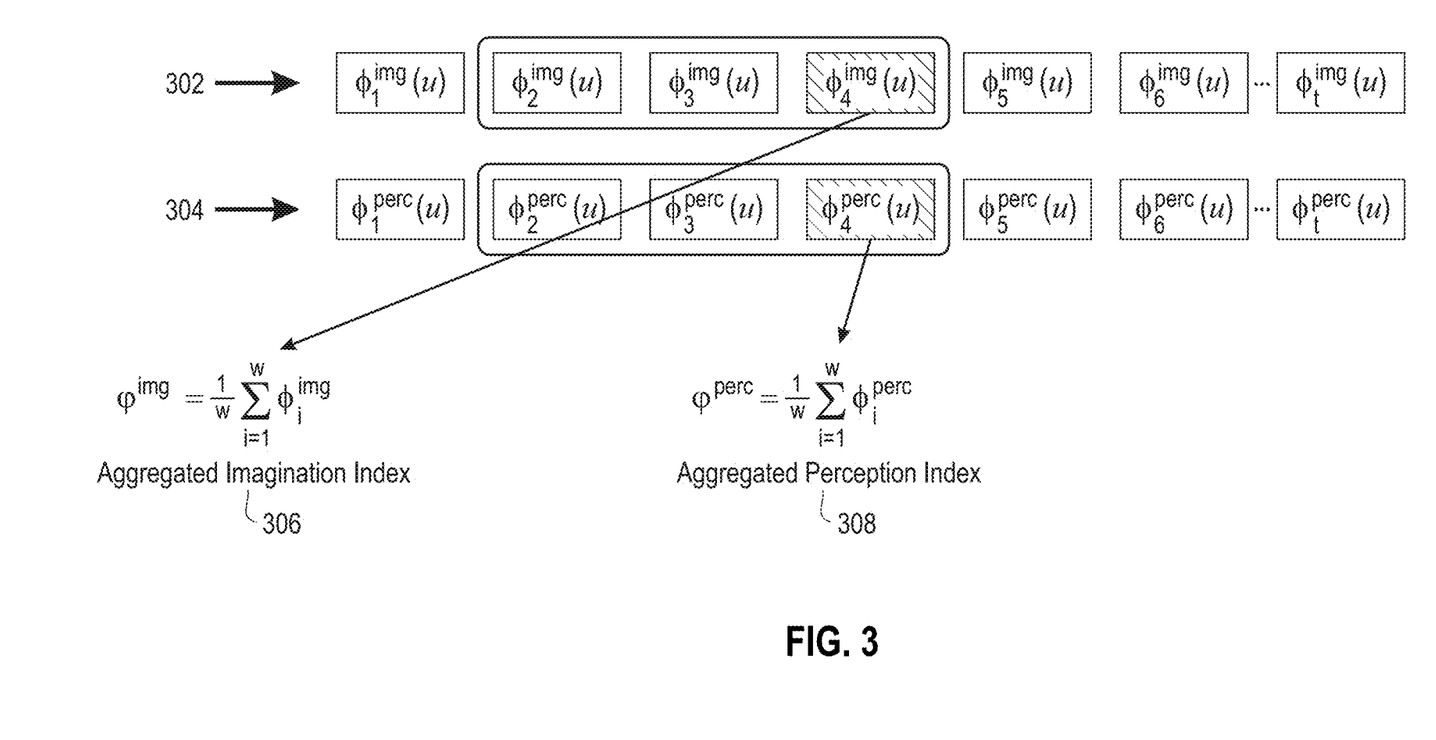
FIG. 3 is a diagram illustrating estimating a perception index and an imagination index of a user, according to an exemplary embodiment of the invention.

FIG. 3 is a diagram illustrating estimating a perception index and an imagination index of a user, according to an exemplary embodiment of the invention. By way of illustration, FIG. 3 depicts element 302, which shows an estimation of an aggregated imagination index 306 over a window w (for example, a window size of three, as illustrated in FIG. 3). Additionally, FIG. 3 depicts element 304, which shows an estimation of an aggregated perception index 308 over window w. Accordingly, FIG. 3 illustrates the computation of an aggregated perception index and an aggregated imagination index computation. In one or more embodiments of the invention, the aggregated indices are averaged over time window w, and the system estimates the aggregated metrics by considering the user's engagement over the time window w.

Figure 4:
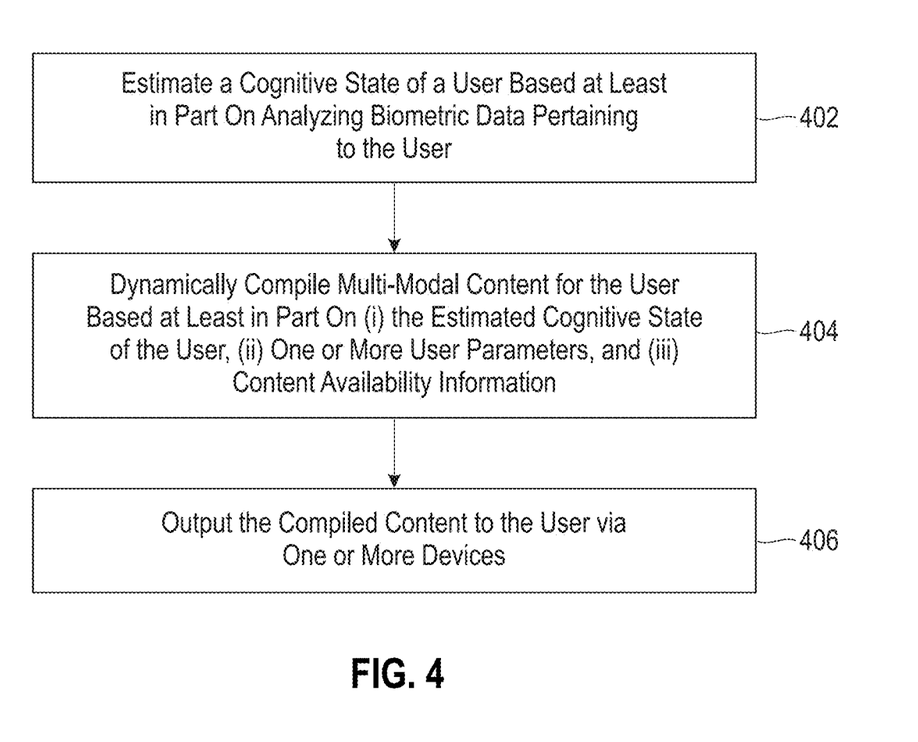
FIG. 4 is a flow diagram illustrating techniques according to an embodiment of the invention.

FIG. 4 is a flow diagram illustrating techniques according to an embodiment of the present invention. Step 402 includes estimating a cognitive state of a user based at least in part on analyzing one or more sets of biometric data pertaining to the user. Estimating the cognitive state of the user can include determining (i) an imagination index attributed to the user and (ii) a perception index attributed to the user. Additionally, the one or more sets of biometric data can include eye gaze data, brain signal data, and/or body movement data.

Step 404 includes dynamically compiling multi-modal content for the user based at least in part on (i) the estimated cognitive state of the user, (ii) one or more user parameters, and (iii) content availability information. The one or more user parameters can include user engagement information, one or more user models, and/or user pedagogy information. Additionally, the multi-modal content can include text content, audio content, video content, augmented reality content, and/or virtual reality content.

Step 406 includes outputting the compiled content to the user via one or more devices. Such devices can include, for example, computer devices, mobile devices, tablets, gaming devices, VR devices, AR devices, etc.

Also, an additional embodiment of the invention can include estimating the cognitive state of the user by learning at least one classifier based at least in part on one or more biometric data feature representations, and applying the at least one classifier to the one or more sets of biometric data.

The techniques depicted in FIG. 4 can also, as described herein, include providing a system, wherein the system includes distinct software modules, each of the distinct software modules being embodied on a tangible computer-readable recordable storage medium. All of the modules (or any subset thereof) can be on the same medium, or each can be on a different medium, for example. The modules can include any or all of the components shown in the figures and/or described herein. In an embodiment of the invention, the modules can run, for example, on a hardware processor. The method steps can then be carried out using the distinct software modules of the system, as described above, executing on a hardware processor. Further, a computer program product can include a tangible computer-readable recordable storage medium with code adapted to be executed to carry out at least one method step described herein, including the provision of the system with the distinct software modules.

Additionally, the techniques depicted in FIG. 4 can be implemented via a computer program product that can include computer useable program code that is stored in a computer readable storage medium in a data processing system, and wherein the computer useable program code was downloaded over a network from a remote data processing system. Also, in an embodiment of the invention, the computer program product can include computer useable program code that is stored in a computer readable storage medium in a server data processing system, and wherein the computer useable program code is downloaded over a network to a remote data processing system for use in a computer readable storage medium with the remote system.

An embodiment of the invention or elements thereof can be implemented in the form of an apparatus including a memory and at least one processor that is coupled to the memory and configured to perform exemplary method steps.

Figure 5:
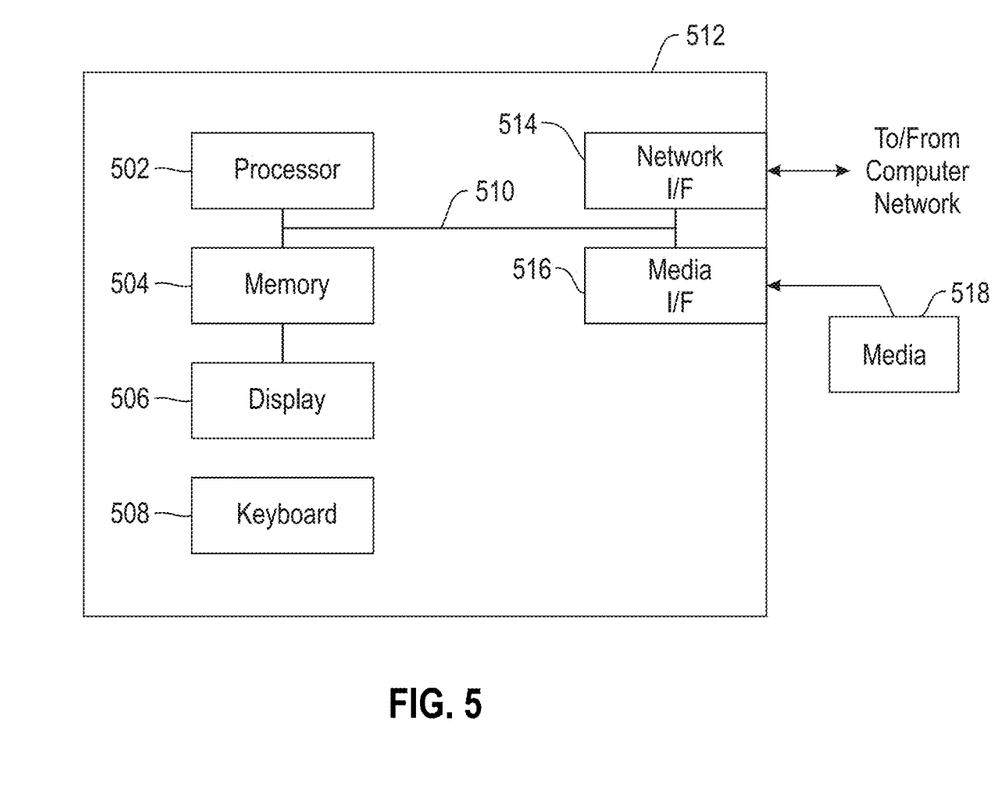
FIG. 5 is a system diagram of an exemplary computer system on which at least one embodiment of the invention can be implemented.

Additionally, an embodiment of the present invention can make use of software running on a computer or workstation. With reference to FIG. 5, such an implementation might employ, for example, a processor 502, a memory 504, and an input/output interface formed, for example, by a display 506 and a keyboard 508. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, a mechanism for inputting data to the processing unit (for example, mouse), and a mechanism for providing results associated with the processing unit (for example, printer). The processor 502, memory 504, and input/output interface such as display 506 and keyboard 508 can be interconnected, for example, via bus 510 as part of a data processing unit 512. Suitable interconnections, for example via bus 510, can also be provided to a network interface 514, such as a network card, which can be provided to interface with a computer network, and to a media interface 516, such as a diskette or CD-ROM drive, which can be provided to interface with media 518.

Accordingly, computer software including instructions or code for performing the methodologies of the invention, as described herein, may be stored in associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 502 coupled directly or indirectly to memory elements 504 through a system bus 510. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including, but not limited to, keyboards 508, displays 506, pointing devices, and the like) can be coupled to the system either directly (such as via bus 510) or through intervening I/O controllers (omitted for clarity).

Network adapters such as network interface 514 may also be coupled to the system to enable the data processing system to become coupled to other data processing systems or remote printers or storage devices through intervening private or public networks. Modems, cable modems and Ethernet cards are just a few of the currently available types of network adapters.

As used herein, including the claims, a "server" includes a physical data processing system (for example, system 512 as shown in FIG. 5) running a server program. It will be understood that such a physical server may or may not include a display and keyboard.

The present invention may be a system, a method, and/or a computer program product at any possible technical detail level of integration. The computer program product may include a computer readable storage medium (or media) having computer readable program instructions thereon for causing a processor to carry out embodiments of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform embodiments of the present invention.

Embodiments of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It should be noted that any of the methods described herein can include an additional step of providing a system comprising distinct software modules embodied on a computer readable storage medium; the modules can include, for example, any or all of the components detailed herein. The method steps can then be carried out using the distinct software modules and/or sub-modules of the system, as described above, executing on a hardware processor 502. Further, a computer program product can include a computer-readable storage medium with code adapted to be implemented to carry out at least one method step described herein, including the provision of the system with the distinct software modules.

In any case, it should be understood that the components illustrated herein may be implemented in various forms of hardware, software, or combinations thereof, for example, application specific integrated circuit(s) (ASICS), functional circuitry, an appropriately programmed digital computer with associated memory, and the like. Given the teachings of the invention provided herein, one of ordinary skill in the related art will be able to contemplate other implementations of the components of the invention.

Additionally, it is understood in advance that implementation of the teachings recited herein are not limited to a particular computing environment. Rather, embodiments of the present invention are capable of being implemented in conjunction with any type of computing environment now known or later developed.

For example, cloud computing is a model of service delivery for enabling convenient, on-demand network access to a shared pool of configurable computing resources (for example, networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (for example, country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (for example, storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (for example, web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (for example, host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (for example, mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (for example, cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
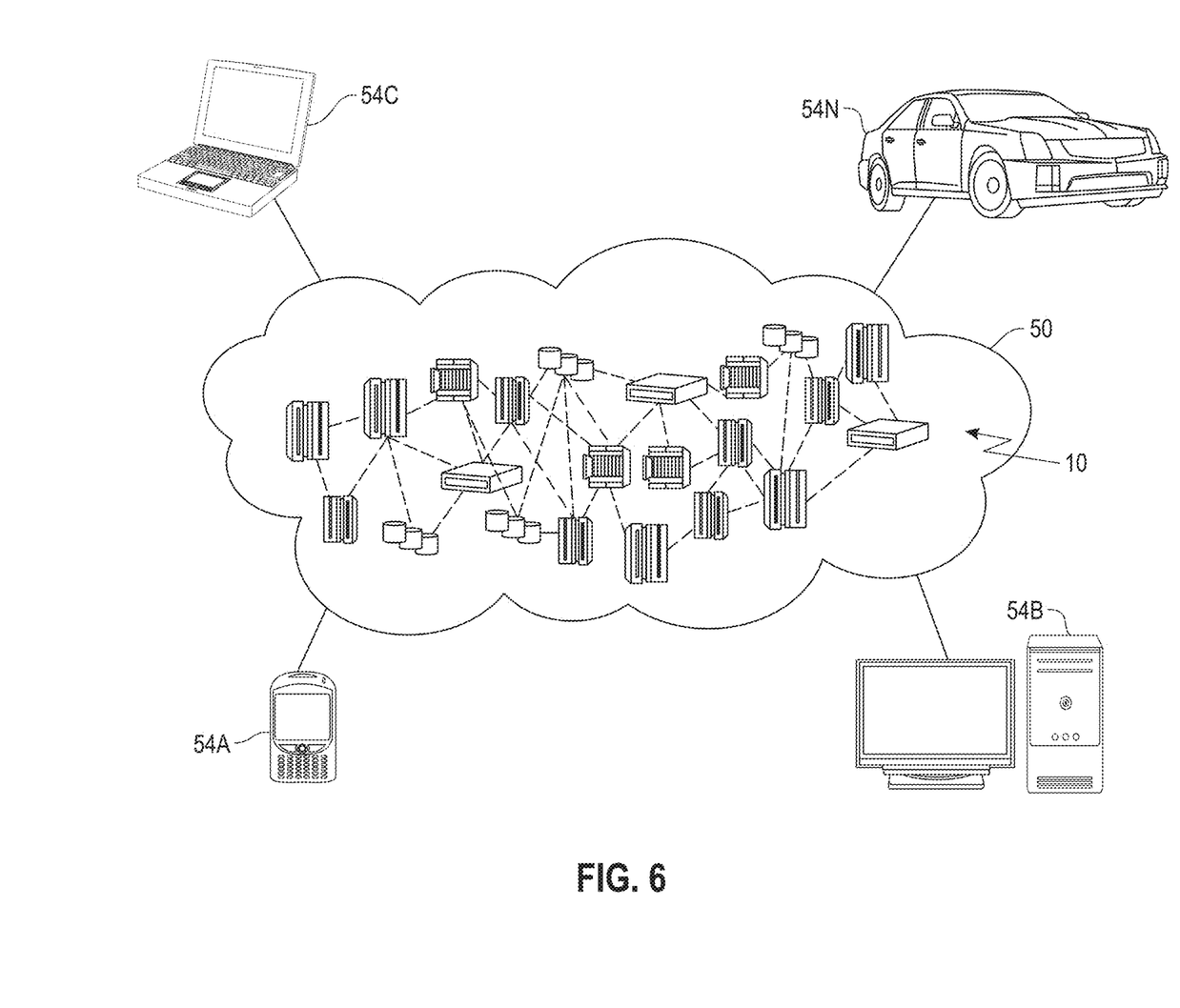
FIG. 6 depicts a cloud computing environment according to an embodiment of the present invention.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 7:
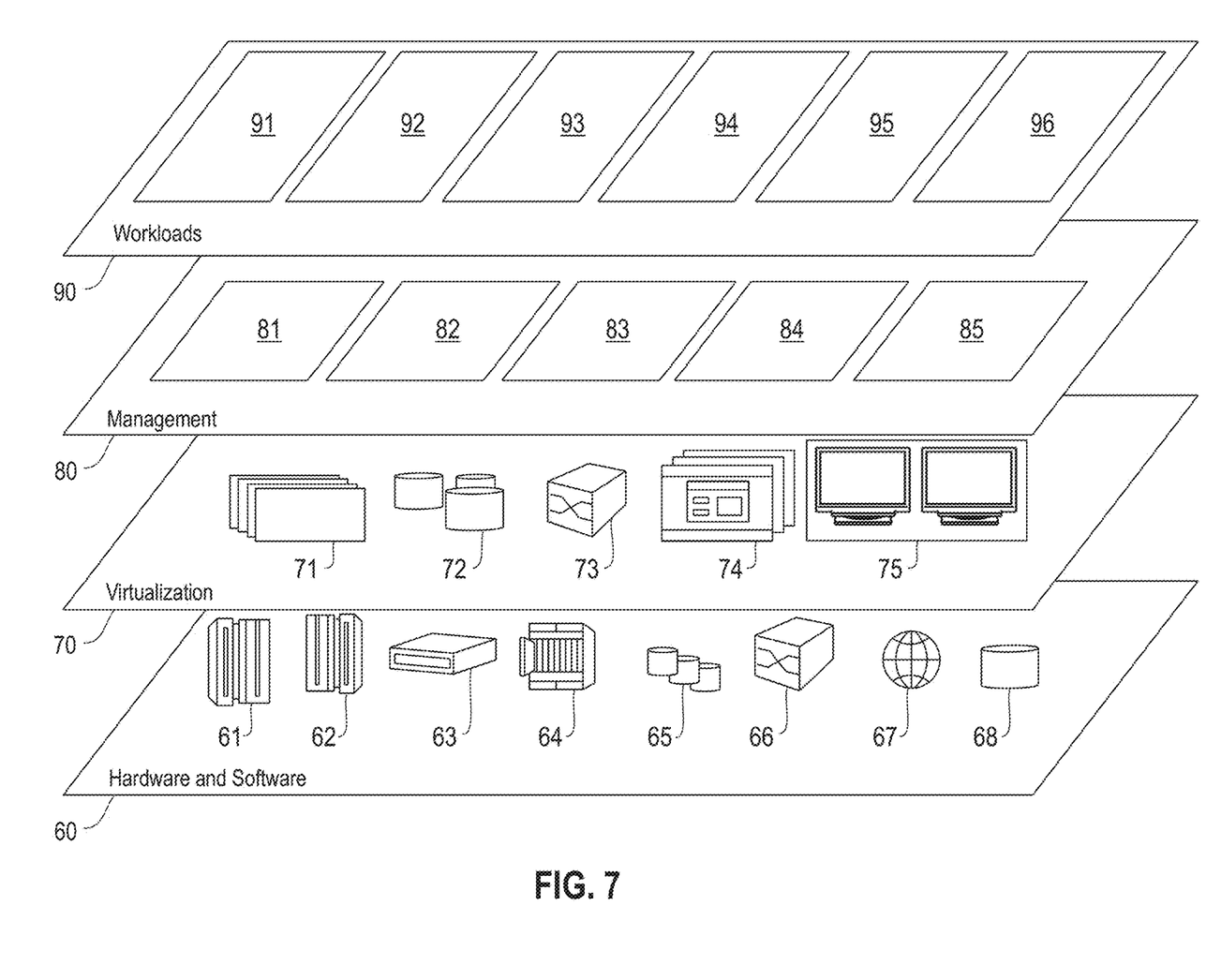
FIG. 7 depicts abstraction model layers according to an embodiment of the present invention.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75. In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources.

In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and content marshaling 96, in accordance with the one or more embodiments of the present invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, estimating the cognitive state of a user based at least in part on biometric data analysis, and dynamically marshaling content for the user based on the user's estimated cognitive state.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, the method comprising:
    estimating a cognitive state of a user based at least in part on analyzing sets of biometric data pertaining to the user, wherein the sets of biometric data comprise (i) eye gaze data derived from one or more cameras focused on a the user, (ii) brain signal data derived from electroencephalography brainwave data, and (iii) body movement data derived from an accelerometer sensor-enabled smart wearable worn by the user;
    dynamically compiling multi-modal content for the user based at least in part on:
        (i) the estimated cognitive state of the user,
        (ii) content availability information, and
        (iii) multiple user parameters consisting:
            user engagement information comprising an average session length metric,
            a diligence score metric based at least in part on (a) login frequency, (b) average session length and (c) length of content video,
            a reflective score metric based at least in part on a number of rewind events,
            an impatience score metric based at least in part on a number of forward seek events, a completion amount metric,
a user-specific model comprising multiple content type difficulty preferences, cognitive load information, user device resource information, user budget information, temporal information, user mood information, user mastery level information with respect to multiple types of content, and
user pedagogy information comprising identification of known and unknown concepts for the user, and identification of user preferences with respect to depth-first searching and breadth-first searching content exploration; and
outputting the compiled content to the user via one or more devices;
wherein the method is carried out by at least one computing device.

2. The computer-implemented method of claim 1, wherein said estimating the cognitive state of the user comprises determining (i) an imagination index attributed to the user and (ii) a perception index attributed to the user.

3. The computer-implemented method of claim 1, wherein the multi-modal content comprises text content.

4. The computer-implemented method of claim 1, wherein the multi-modal content comprises audio content.

5. The computer-implemented method of claim 1, wherein the multi-modal content comprises video content.

6. The computer-implemented method of claim 1, wherein the multi-modal content comprises augmented reality content.

7. The computer-implemented method of claim 1, wherein the multi-modal content comprises virtual reality content.

8. A computer program product comprising a computer readable storage medium having program instructions embodied therewith, the program instructions executable by a computing device to cause the computing device to:
estimate a cognitive state of a user based at least in part on analyzing sets of biometric data pertaining to the user, wherein the sets of biometric data comprise (i) eye gaze data derived from one or more cameras focused on a the user, (ii) brain signal data derived from electroencephalography brainwave data, and (iii) body movement data derived from an accelerometer sensor-enabled smart wearable worn by the user;
dynamically compile multi-modal content for the user based at least in part on:
(i) the estimated cognitive state of the user,
(ii) content availability information, and
(iii) multiple user parameters consisting:
user engagement information comprising an average session length metric,
a diligence score metric based at least in part on (a) login frequency, (b) average session length and (c) length of content video,
a reflective score metric based at least in part on a number of rewind events,
an impatience score metric based at least in part on a number of forward seek events,
a completion amount metric,
a user-specific model comprising multiple content type difficulty preferences, cognitive load information, user device resource information, user budget information, temporal information, user mood information, user mastery level information with respect to multiple types of content, and
user pedagogy information comprising identification of known and unknown concepts for the user, and identification of user preferences with respect to depth-first searching and breadth-first searching content exploration; and
output the compiled content to the user via one or more devices.

9. The computer program product of claim 8, wherein the multi-modal content comprises at least one of (i) text content, (ii) audio content, (iii) video content, (iv) augmented reality content, and (v) virtual reality content.

10. A system comprising:
a memory; and
at least one processor operably coupled to the memory and configured for:
estimating a cognitive state of a user based at least in part on analyzing sets of biometric data pertaining to the user, wherein the sets of biometric data comprise (i) eye gaze data derived from one or more cameras focused on a the user, (ii) brain signal data derived from electroencephalography brainwave data, and (iii) body movement data derived from an accelerometer sensor-enabled smart wearable worn by the user;
dynamically compiling multi-modal content for the user based at least in part on:
(i) the estimated cognitive state of the user,
(ii) content availability information, and
(iii) multiple user parameters consisting:
user engagement information comprising an average session length metric,
a diligence score metric based at least in part on (a) login frequency, (b) average session length and (c) length of content video,
a reflective score metric based at least in part on a number of rewind events,
an impatience score metric based at least in part on a number of forward seek events,
a completion amount metric,
a user-specific model comprising multiple content type difficulty preferences, cognitive load information, user device resource information, user budget information, temporal information, user mood information, user mastery level information with respect to multiple types of content, and
user pedagogy information comprising identification of known and unknown concepts for the user, and identification of user preferences with respect to depth-first searching and breadth-first searching content exploration; and
outputting the compiled content to the user via one or more devices.

* * * * *